(12) United States Patent
Haselton et al.

(10) Patent No.: US 9,869,675 B2
(45) Date of Patent: Jan. 16, 2018

(54) LOW RESOURCE PROCESSOR USING SURFACE TENSION VALVES FOR EXTRACTING, CONCENTRATING, AND DETECTING WHOLE CELLS

(71) Applicant: Vanderbilt University, Nashville, TN (US)

(72) Inventors: Rick Haselton, Nashville, TN (US); David Wright, Nashville, TN (US); Joseph Conrad, Nashville, TN (US); Nick Adams, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 123 days.

(21) Appl. No.: 14/201,097

(22) Filed: Mar. 7, 2014

(65) Prior Publication Data

US 2014/0272937 A1 Sep. 18, 2014

Related U.S. Application Data

(60) Provisional application No. 61/780,361, filed on Mar. 13, 2013.

(51) Int. Cl.
| | |
|---|---|
| *G01N 33/543* | (2006.01) |
| *G01N 33/569* | (2006.01) |
| *B01L 3/00* | (2006.01) |
| *G01N 35/00* | (2006.01) |

(52) U.S. Cl.
CPC .. *G01N 33/56966* (2013.01); *B01L 3/502738* (2013.01); *B01L 3/502761* (2013.01); *G01N 33/54326* (2013.01); *G01N 35/0098* (2013.01); *B01L 2200/0647* (2013.01); *B01L 2200/0668* (2013.01); *B01L 2300/087* (2013.01); *B01L 2300/0838* (2013.01); *B01L 2400/0688* (2013.01)

(58) Field of Classification Search
None
See application file for complete search history.

(56) References Cited

U.S. PATENT DOCUMENTS

| | | | |
|---|---|---|---|
| 7,521,261 B2 | 4/2009 | Haselton | |
| 2004/0053337 A1* | 3/2004 | Yamazaki | C12Q 1/18 435/7.1 |
| 2004/0248093 A1* | 12/2004 | Coombs | B01L 3/502761 435/6.11 |

(Continued)

FOREIGN PATENT DOCUMENTS

| | | |
|---|---|---|
| WO | WO 2009/044088 | 4/2009 |
| WO | WO 2009/111316 | 9/2009 |

(Continued)

OTHER PUBLICATIONS

Berry et al., Purification of cell subpopulations via immiscible filtration assisted by surface tension (IFAST), 2011, 13(6), 1033-1042.*

(Continued)

*Primary Examiner* — Erik B Crawford
(74) *Attorney, Agent, or Firm* — Parker Highlander PLLC

(57) ABSTRACT

Systems and methods are described for isolation, separation and detection of a molecular species using a low resource device for processing of samples. Methods include isolation, separation and detection of whole cells.

16 Claims, 13 Drawing Sheets

(56) References Cited

U.S. PATENT DOCUMENTS

| | | | |
|---|---|---|---|
| 2006/0003439 A1 | 1/2006 | Ismagilov et al. | |
| 2006/0252031 A1* | 11/2006 | Abbott | B01L 3/502761 435/5 |
| 2013/0183678 A1 | 7/2013 | Haselton | |

FOREIGN PATENT DOCUMENTS

| | | |
|---|---|---|
| WO | WO 2010/077859 | 7/2010 |
| WO | WO 2012009627 A1 * | 1/2012 |

OTHER PUBLICATIONS

Office Action issued in Chinese Application No. 201180044832.8, dated Jun. 10, 2014.
Chen et al., "An integrated, self-contained microfluidic cassette for isolation, amplification, and detection of nucleic acids", *Biomed. Microdevices*, 12(4):705-719, 2010.
Hagan et al., "An integrated, valveless system for microfluidic purification and reverse transcription-PCR amplification of RNA for detection of infectious agents", *Lab. Chip.*, 11(5):957-61, 2011.
Niemz et al., "Point-of-care nucleic acid testing for infectious diseases", *Trends Biotechnol.*, 29(5):240-250, 2011.
PCT International Preliminary Report on Patentability issued in International Application No. PCT/US2011/044167, dated Jan. 31, 2013.
PCT International Search Report and Written Opinion issued in International Application No. PCT/US2011/044167, dated Jan. 11, 2012.
Price et al., "Nucleic acid extraction techniques and application to the microchip", *Lab. Chip.*, 9(17):2484-2494, 2009.
Adams et al., "Design criteria for developing low-resource magnetic bead assays using surface tension valves", *Biomicrofluidics*, 7(1): 14104, 2013.
Bull et al., "Defining blood processing parameters for optimal detection of cryopreserved antigen-specific responses for HIV vaccine trials", *J. Immunol. Methods*, 322:57-69 (2007).
Cox et al., "Cellular Immune assays for evaluation of Vaccine efficacy in developing countries. Manual of Clinical laboratory Immunology", in *Manual of Molecular and Clinical Laboratory Immunology*, Detrick et al. Eds. (6th ed.) p. 301-315 (2002).
HANC-LAB-P0001v5.2, Effective date Sep. 22, 2014 p. 30 of 41 Cross-Network PBMC Processing Standard Operating Procedure.
Immunovirology Research Network (IVRN) Laboratory Manual: Separation and storage of serum, plasma and PBMCs. IVRN. First dated Dec. 12, 1007.
Islam et al., "Peripheral blood cells preparation influences the level of expression of leukocyte cell surface markers as assessed with quantitative multicolor flow cytometry", *Cytometry*, 22:128-134 (1995).
Kierstead et al., "Enhanced rates and magnitude of immune responses detected against an HIV vaccine: effect of using an optimized process for isolating PBMC", *AIDS Res Hum Retroviruses*, 23:86-92 (2007).
Shearer et al., "Lymphocyte subsets in healthy children from birth through 18 years of age: the Pediatric AIDS Clinical Trials Group P1009 study", *J Allergy Clin Immunol.*, 112(5):973-80 (2003).
Sigma-Aldrich Accuspin™ System-Histopaque®-1077, procedure No. A6929/A7054/A0561, first Dated Sep. 2003.
Weinberg et al., "Effect of shipment, storage, anticoagulant, and cell separation on lymphocyte proliferation assays for human immunodeficiency virus-infected patients", *Clin. Diagn. Lab. Immunol.*, 5:804-807 (1998).
Weinvberg et al., "Optimization of storage and shipment of cryopreserved peripheral blood mononuclear cells from HIV-infected and uninfected individuals for ELISPOT assays", *J Immunol Methods.*, 363(1):42-50 (2010).

* cited by examiner

LOW RESOURCE PROCESSOR USING SURFACE TENSION VALVES FOR EXTRACTING, CONCENTRATING, AND DETECTING WHOLE CELLS

The present application claims benefit of priority to U.S. Provisional Application Ser. No. 61/780,361, filed Mar. 13, 2013, the entire contents of which are hereby incorporated by reference.

The invention was made with government support under Grant No. DGE 0909667 awarded by the National Science Foundation. The government has certain rights in the invention.

BACKGROUND OF THE INVENTION

1. Field of the Invention

The invention relates generally to the field of diagnostics and detection. More particularly, the invention relates to low resource processors for assessing molecular interactions. Specifically, the invention relates to the use of devices containing multiple chambers separated by surface tension valves for the processing of microbeads having screening reagents attached thereto. The device permits assaying for the content of a wide variety of environmental and biological samples, including whole cells.

2. Description of Related Art

Recent research has focused on the development of nucleic acid-based detection for low resource settings (Niemz et al., 2011). Nucleic acid-based detection systems, such as quantitative PCR (qPCR), are particularly attractive technologies for detection of pathogens because of their sensitivity, specificity and relatively rapid time-to-answer. The effectiveness of PCR is dependent on both the quality and quantity of nucleic acid template (Beuselinck et al., 2005) and the absence of interferents (Radstrom et al., 2004). For example, carbohydrates, proteins, lipids or other unidentified interferents present in clinical samples have all been shown to inhibit PCR and produce false negatives (Monteiro et al., 1997; Wilson, 1997; Coiras et al., 2003). In addition to various interferents, patient samples also contain nucleases, which directly reduce the number of nucleic acid targets present (Wilson, 1997).

To minimize false negatives and maximize the efficiency of nucleic acid-based diagnostics, nucleic acids are extracted and concentrated into an interferent-free buffer prior to testing. Several solid phase extraction kits are commercially available to purify DNA or RNA from patient samples. Many of these kits rely on selective nucleic acid binding to silica-coated surfaces in the presence of ethanol and a chaotropic agent, such as guanidinium thiocyanate (GuSCN) (Avison, 2007; Yamada et al., 1990). These kits are not cost effective for low resource use and often require the use of specialized laboratory equipment, such as a robot or centrifuge, and trained technicians that are unavailable in a low resource setting.

Microfluidics is one promising format for low resource cell-based diagnostics. Recently, there has been a growing interest in expanding microfluidic technologies for sample preparation (Niemz et al., 2011; Price et al., 2009). Many of these devices are suitable for integrating with downstream nucleic acid amplification and detection technologies (Chen et al., 2010; Hagan et al., 2011). However, the small surface area of solid phase available for cell binding and the limited sample volume that can be flowed through the channels limit the total mass of material recovered (Niemz et al., 2011), and therefore negatively impact the limit of detection.

Similar issues relate to the testing for many species of interest, including proteins, lipids, carbohydrates, and whole cells. Therefore, a rapid, noninvasive diagnostic technology for the isolation of whole cells is desirable, especially in low resource environments. Such technology would allow for blood cell profiling and the isolation and detection of cells to aid in cancer detection and to monitor disease progression and response to therapy for diseases such as HIV.

SUMMARY OF THE INVENTION

Thus, in accordance with the present invention, there is provided a method of processing a cell-containing sample comprising (a) providing a device comprising a plurality of sequential chambers each comprising a fluid and separated by surface tension valves, wherein a first reaction chamber comprises a particle having a reactant on its surface; (b) introducing into said first reaction chamber a sample comprising at least one whole cell; (c) incubating said first reaction chamber under conditions sufficient to permit reaction of said reactant with said at least one whole cell; (d) transporting said particle from said first reaction chamber into at least a second chamber; and (e) detecting interaction of said at least one whole cell with said reactant. Other chambers include an elution chamber and/or a concentration chamber. The device may comprise at least three chambers, such as a first reaction chamber, a first processing chamber and a first detection chamber, wherein said first processing chamber is disposed between said first reaction chamber and said first detection chamber. The method may also further comprise reversing the transport of said particle to reintroduce said particle into a chamber through which it has already passed. In some embodiments, the target molecular species are separated from the beads in the final chamber. These targets are then further analyzed such as an immunoassay, a flow cytometry assay, a microscopy assay, a RT-PCR reaction, or a PCR reaction. The method may be automated. In one aspect, the method may isolate a portion of cell membrane rather than a whole cell.

The device may comprise continuous tubing and surface tension valves separating said tubing into said plurality of chambers. The tubing may be made of glass, a polymer or a metal. The tubing may comprise an inner surface coated by a polymer. The particle may be a magnetic particle, a paramagnetic particle or a non-magnetic particle having a density of different than the surrounding fluid. Transporting may comprise passing a magnetic field along said tubing or subjecting said tubing to distinct intermittent magnetic fields to effect movement of said particle. Transporting may instead comprise applying centrifugal force to said device such that said particle is transported through said plurality of chambers. Alternatively, one can perform processing using gravitational settling with a high density bead (optionally magnetic) contained in a lower density fluid, or buoyancy forces that arise from a low density particle contained within a higher density liquid.

The whole cell may be a protist, an animal cell, or a plant cell. The whole cell may be living or fixed. The protist may be of the genus *Plasmodium, Babesia, Leishmania, Giardia,* or *Trypanosoma*. The animal cell may be a mammalian cell. The mammalian cell may be a human cell. In certain aspects, the human cell may be a CD4+ T cell, a virus-infected cell, a parasite-infected cell, a cancer cell, or a blood cell. The reactant may be an antibody, an aptamer, or a cell surface receptor ligand.

Detecting the interaction of said cell with said reactant may comprise FRET, colorimetric assay, fluorescence assay, spectrophotometry, RT-PCR, change in optical density, or change in refractive index. Introducing may comprise injecting said sample through a wall of said first reaction chamber. To facilitate introduction, the wall of said first reaction chamber may comprise a port facilitating injection of said sample. Samples can also load by "capillary" action, meaning transfer of fluid into a bundle of small diameter capillary tubes.

The sample may be a biological sample, such as a tissue or fluid sample obtained from a patient. Examples of fluid samples include, but are not limited to, stool, blood, urine, sputum, and saliva. The sample may be an environmental sample such as a soil sample, a water sample, or a plant sample. The sample may be fixed. The particle may be 0.1 to 10 micrometers in diameter, and the tubing may be 0.5 to $10^4$ micrometers inner diameter.

The surface tension valve may comprise a non-reactive gas or a fluid having low vapor pressure or low surface tension, such as a non-reactive gas like air, carbon dioxide, nitrogen, argon, helium, or sulfur hexafluoride, or a fluid like mineral oil, Dodecane, 1-Dodecene, Tridecane, Methyloleate, Acetophenone, Propyl Benzoate, or 1-Methylnaphthalene.

The first reaction chamber may comprise a known quantity of phantom cells used to back calculate the quantity of unknown whole cells in the original sample based on the efficiency of the processing as quantifying based on the extraction of said phantom cells. The term "phantom cell" is a structure that mimics a cell by virtue of its size and density, containing a known surface marker(s), and is capable of detection according to the assay, optionally in a different "channel" (i.e., optical channel). Alternatively, the sample may be spiked with a known quantity of phantom cells prior to introduction into the first reaction chamber. The isolation of the phantom cell ensures that the device is functioning and also provides a means to quantify the efficiency of processing, which can be used to calculate the number of unknown whole cells in the original sample. Such phantom cells may be fluorescently-labeled beads that are bound by the target of the reactant (e.g., CD4), thereby ensuring that the phantom cells will interact with the reactant. Such phantom cells may be fluorescently-labeled liposomes comprising the target of the reactant on their surface. Preferably, the phantom cells are gold-plated polystyrene beads containing the target of the reactant on their surface.

The method may be a method of multiplex detection wherein said first reaction chamber further comprises a second particle having a second reactant on its surface; said sample further comprises an analyte; said incubating further permits reaction of said second reactant with said analyte; and said detecting further detects interaction between said second reactant and said analyte.

The analyte may be a protein, a polypeptide, a lipid, a carbohydrate, a nucleic acid, a heavy metal, an organochemical compound, a bacterium, a virus, or a fungal cell. The protein may be an antigen, an antibody, or an enzyme. The analyte may be a second whole cell. The reactant may be an antibody, an antigen, a chelating agent, a lipid, a carbohydrate, a metal, an organochemical compound, an enzyme substrate, or a nucleic acid. Detecting the interaction of said analyte with said reactant may comprise FRET, colorimetric assay, fluorescence assay, RT-PCR, change in optical density, or change in refractive index.

In yet another embodiment, there is provided a method of processing a cell-containing sample comprising (a) providing a device comprising a plurality of sequential chambers each comprising a fluid and separated by surface tension valves; (b) introducing into said first chamber a particle comprising a surface reactant, the surface of which comprises at least one whole cell bound to said reactant; (c) transporting said particle from said first chamber into at least a second chamber; and (d) detecting the presence of said at least one whole cell. The method may further comprise mixing said particle with a sample to permit binding of said at least one whole cell to said reactant on said particle. The particle may be a magnetic particle, a paramagnetic particle or a non-magnetic particle having a density different than the surrounding fluid. Transporting may comprise passing a magnetic field along said tubing or subjecting said tubing to distinct intermittent magnetic fields to effect movement of said particle. Transporting may instead comprise applying centrifugal force to said device such that said particle is transported through said plurality of chambers, or by density driven transport, e.g., a very dense particle falling through a less dense liquid, or a less dense buoyant particle rising within a more dense liquid. The method may be automated. In one aspect, the method may isolate a portion of cell membrane rather than a whole cell.

The whole cell may be a protist, an animal cell, or a plant cell. The whole cell may be living or fixed. The protist may be of the genus *Plasmodium, Babesia, Leishmania, Giardia*, or *Trypanosoma*. The animal cell may be a mammalian cell. The mammalian cell may be a human cell. In certain aspects, the human cell may be a CD4+ T cell, a virus-infected cell, a parasite-infected cell, a cancer cell, or a blood cell. The reactant may be an antibody, an aptamer, or a cell surface receptor ligand.

Detecting the interaction of said analyte with said reactant may comprise FRET, colorimetric assay, fluorescence assay, spectrophotometry, RT-PCR, change in optical density, or change in refractive index. Introducing may comprise injecting said sample through a wall of said first reaction chamber. To facilitate introduction, the wall of said first reaction chamber may comprise a port facilitating injection of said sample.

The sample may be a biological sample, such as a tissue or fluid sample obtained from a patient. Examples of fluid samples include, but are not limited to, stool, blood, urine, sputum, and saliva. The sample may be an environmental sample such as a soil sample, a water sample, or a plant sample. The sample may be fixed. The particle may be 0.1 to 10 micrometers in diameter, and the tubing may be 0.5 to $10^4$ micrometers inner diameter. The device may comprise at least three chambers, such as a first reaction chamber, a first processing chamber and a first detection chamber, wherein said first processing chamber is disposed between said first reaction chamber and said first detection chamber.

The surface tension valve may comprise a non-reactive gas or a fluid having low vapor pressure or low surface tension, such as a non-reactive gas like air, carbon dioxide, nitrogen, argon, helium, or sulfur hexafluoride, or a fluid like mineral oil, Dodecane, 1-Dodecene, Tridecane, Methyloleate, Acetophenone, Propyl Benzoate, or 1-Methylnaphthalene.

The first reaction chamber may comprise a known quantity of phantom cells used to back calculate the quantity of unknown whole cells in the original sample based on the efficiency of the processing as quantifying based on the extraction of said phantom cells. Alternatively, the sample may be spiked with a known quantity of phantom cells prior to introduction into the first reaction chamber. The isolation of the phantom cell ensures that the device is functioning and also provides a means to quantify the efficiency of processing, which can be used to calculate the number of unknown whole cells in the original sample. Such phantom cells may be fluorescently-labeled plastic beads that are bound by the target of the reactant (e.g., CD4), thereby ensuring that the phantom cells will interact with the reactant. Such phantom cells may be fluorescently-labeled liposomes comprising the target of the reactant on their surface. Preferably, the phantom cells are gold-plated polystyrene beads containing the target of the reactant on their surface.

The method may be a method of multiplex detection wherein said first reaction chamber further comprises a second particle having a second reactant on its surface; said sample further comprises an analyte; said incubating further permits reaction of said second reactant with said analyte; and said detecting further detects interaction between said second reactant and said analyte.

The analyte may be a protein, a polypeptide, a lipid, a carbohydrate, a nucleic acid, a heavy metal, an organochemical compound, a bacterium, a virus, or a fungal cell. The protein may be an antigen, an antibody, or an enzyme. The reactant may be an antibody, an antigen, a chelating agent, a lipid, a carbohydrate, a metal, an organochemical compound, an enzyme substrate, or a nucleic acid. Detecting the interaction of said analyte with said reactant may comprise FRET, colorimetric assay, fluorescence assay, RT-PCR, change in optical density, or change in refractive index.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
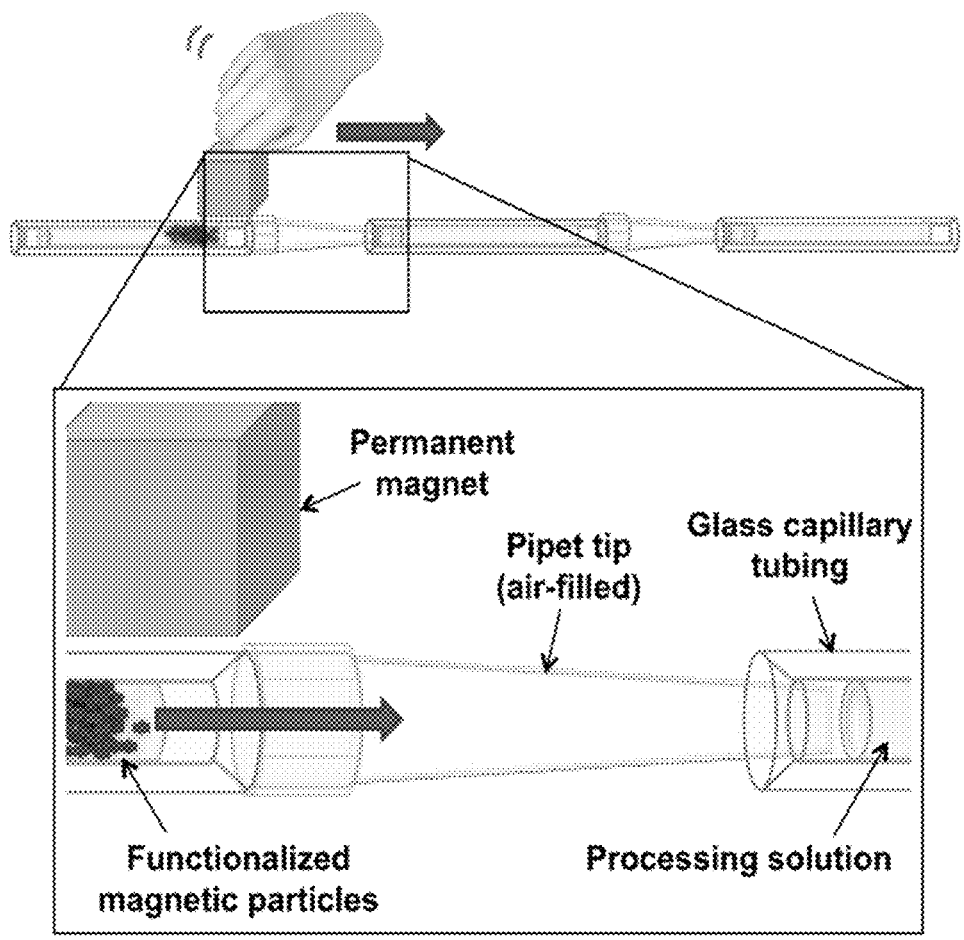
FIG. 1—Design of the prototype extraction method showing three processing solutions held in place in glass tubing and separated by air-filled pipette tips. RNA is adsorbed to silica-coated magnetic particles which are pulled left to right through successive processing chambers using an external magnet. Following processing, the RNA is eluted in a final water chamber.

As discussed above, CD4+ T cell count is a critical diagnostic measure in HIV disease management and remains a standard metric to assess immune function and HIV disease progression. Clinical diagnostic tests are moving to the point-of-care, and with about 70% of HIV infections occurring in sub-Saharan Africa, tests are needed that can be readily implemented in a low resource setting. CD4+ T cell counts will be relied upon as antiretroviral therapy, maternal and child health, and prevention of mother to child transmission programs expand.

As discussed above, a major impediment to the use of simple and rapid assays for detecting whole cells is the need for laboratory equipment, such as centrifuges and pipettes, which require trained personnel to operate and which are not available in the field. The overall goal is to develop a self-contained low resource device to extract species of interest, such as whole cells, from samples and concentrate the targets in an elution buffer that can be used in a variety of downstream applications without the need for complicated or expensive methodologies.

The inventors have developed an alternative whole cell extraction cassette suitable for operation in a low resource setting. This self-contained extraction cassette is preloaded with processing solutions separated by air gaps, which are referred to as "surface tension valves." In whole cell extraction studies, CD4+ T cells are selectively adsorbed to antibody-coated magnetic particles. Individual processing solutions are preloaded into a single continuous length of Tygon tubing and are separated from one another and held in place by surface tension forces. Removal of non-target cells is achieved by selective CD4 adsorption to antibody-coated magnetic particles which are then pulled through each processing solution using an externally applied magnetic field. CD4+ T cells are eluted from the surface of the magnetic particle in the final solution. This report describes the general characteristics of this approach and compares its performance to laboratory-based commercial kits.

The present invention therefore provide a unique solution to problems relating to low cost biomolecular isolation, separation and detection technology, where reactants are rendered "mobile" by disposing them on particles which can be easily manipulated through various "zones" of an apparatus or system. The different zones separate various solutions, including reaction and processing zones. One important aspect of the invention is the use of surface tension valves to segregate the different zones while permitting the transport of the particles through each zone. Surprisingly, the particles can pass through these air valves despite considerable surface tension, and can do so without transferring liquids from one chamber to another. Thus, the present invention can solve many problems currently limiting the application of biomolecular isolation, separation and detection technologies and create new areas of application as well. These and other aspects of the invention are described in greater detail below.

A. The Device

In general, the device will have the following components. First, a continuous tubing will provide the basis for creating a plurality of chambers. The chambers are, in essence, liquid pockets that are maintained separate from each other by the use of surface tension valves, which are fluid or gaseous agents interspersed between the fluid pockets. The device may also include predisposed therein particles for use in detecting analytes that are introduced into the device. Finally, the device may be provided without the liquid pockets, but instead may contain the liquids and fluid/gaseous components in separate containers (i.e., a kit) for use or distribution into/customization of the device at the point of implementation. The individual elements of the device will be discussed in greater detail below.

1. Tubing

Central to the design of this device is the establishment of a series of solutions arrayed along a tube each separated from the next by a surface tension valve. Only tubing of sufficiently small diameter will allow for a stable arrangement of the fluids and valves. Tubing of diameter greater than about 4 mm will not support stable valve formation. Therefore an important physical property of this component is its diameter.

The tubing may be made of a variety of different materials, including glass, polymers or metal. The tubing should be made of, or internally coated with, a polymer that permits formation of surface tension valves, discussed further below. It is also desirable to have tubing with low surface energy, meaning that it is non-binding for proteins, and also hydrophobic. These properties of the tubing material affect the stability of the arrayed solutions and therefore the diameter of the tubing that is useable. Lower surface energy generally will require a tubing of smaller diameter to permit stable valve formation. Typical surface energy values for glass, silanized glass, polystyrene, Teflon and some types of fluorinated ethylene polypropylene Tygon tubing are in the range of 10-50, 10-30, 15-30, 20-30, 5 mN/m, including 10, 15, 18.5, 20, 25, 30, 35, 40, 45 and 50 mN/m.

A particular type of tubing is Tygon tubing, which is a brand name for a variety of flexible tubing. Tygon is a registered trademark of Saint-Gobain Corporation. Tygon tubing is used in many markets including food and beverage, chemical processing, industrial, laboratory, medical, pharmaceutical, and semiconductor processing. There are many formulations of clear, flexible, Tygon tubing. The chemical resistance and physical properties vary among the different formulations, but the tubing generally is considered resistant to almost any chemical attack.

Several formulations of Tygon are Class VI approved and can be used in either surgical procedures or pharmaceutical processing. Medical versions include the following:

Tygon Medical/Surgical Tubing S-50-HL—Characterized to the latest ISO 10993 standards and FDA guidelines for biocompatibility. This material is non-toxic, non-hemolytic, and non-pyrogenic. This formulation is used in minimally invasive devices, dialysis equipment, for bypass procedures, and chemotherapy drug delivery.

Tygon Medical Tubing S-54-HL was introduced in 1964 for use in medical applications. This material can be used in catheters, for intravenous or intra-arterial infusion and other surgical uses. Tygon S-54-HL can also be fabricated into cannulae or protective sheath products using thermoforming and flaring techniques.

Pharmaceutical Tygon includes:

Tygon LFL (Long Flex Life) pump tubing is non-toxic clear tubing with broad chemical resistance. It is often used in product filtration and fermentation and surfactant delivery.

Tygon 2275 High Purity Tubing is a plasticizer-free material that is often used in sterile filling and dispensing systems and diagnostic equipment. This formulation is also considered to have low absorption/adsorption properties, which minimizes the risk of fluid alteration.

Tygon 2275 I.B. High-Purity Pressure Tubing is plasticizer-free and is reinforced with a braid for use with elevated working pressures.

Tygon chemfluor FEP is a non-protein binding tubing that contains no additives or plasticizers. FEP stands for fluorinated ethylene propylene.

Peristaltic applications include the following:

Tygon R-3603 Laboratory Tubing is commonly used in university laboratories. It is often used in incubators, hoods and as a replacement for rubber tubing for Bunsen burners. This material is produced in vacuum sizes and can withstand a full vacuum at room temperature.

Tygon R-1000 Ultra-Soft Tubing is used in general laboratory applications. It is the softest of the Tygon formulations with a durometer hardness of Shore A 40 (ASTM Method D2240-02). Because of the low durometer of this material it is often used in low-torque peristaltic pumps.

Tygon LFL (Long Flex Life) Pump Tubing, Tygon 3350, Tygon S-50-HL Medical/Surgical Tubing, Tygon 2275 High Purity Tubing, and Tygon 2001 Tubing are also used in peristaltic pump applications.

Other types of tubing include the following: Silicone Tubing (LPS), which is the most commonly used peristaltic pump tubing. It provides the longest service life and good chemical compatibility for aqueous solvents. Silicone tubing can be autoclaved a single time using a wet cycle. Vinyl Tubing (LPV) has the lowest per-foot cost of the available peristaltic pump tubing. It generally has only fair compatibility for most aqueous solvents and does not have a good tolerance for organic solvents. It has only about one-third the service live of silicone tubing in a peristaltic pump. Vinyl tubing should not be autoclaved or exposed to temperatures above 80° C. Fluoroelastomer Tubing (LPF) is both the most chemically inert and the shortest lived peristaltic pump tubing. It can even withstand halogenated solvents for a limited time. Its service life is only about one-twentieth that of silicone tubing in a peristaltic pump Like silicone tubing, fluoroelastomer tubing can be autoclaved a single time using a wet cycle. Teflon® Tubing (HPT) is among most inert of all the tubing manufactured. It can withstand nearly any solvent used in a modern laboratory, from distilled water to methylene chloride. Its excellent thermal characteristics allow it to be autoclaved repeatedly. After autoclaving Teflon tubing should not be used for fluid transport until it has cooled. Polyethylene Tubing (HPP) is an inexpensive alternative to Teflon tubing. Like Teflon tubing, polyethylene can handle pressure significantly higher than any of other flexible tubing. Polyethylene does not have the thermal stability of Teflon so it should not be autoclaved; it can, however, be sterilized using ethylene oxide.

2. Chambers

The present inventors have designed processing chambers, equipped with gas/fluid valves, which permit the passage of particles into and out of the chambers without substantial loss of liquids, and preservation of each compartment's integrity. In a particular embodiment, the processing chambers are configured to provide down to nanoliter volumes. Reaction, processing, hybridization, and analysis steps can be conducted in a series of separate chambers. In general, the chambers contain aqueous liquids that contain various chemical and biological species, such as salts, dyes, labels and other chemical species. Examples of the disposition of the chambers and their relationship to one another are illustrated in FIGS. 1-4.

Figure 8:
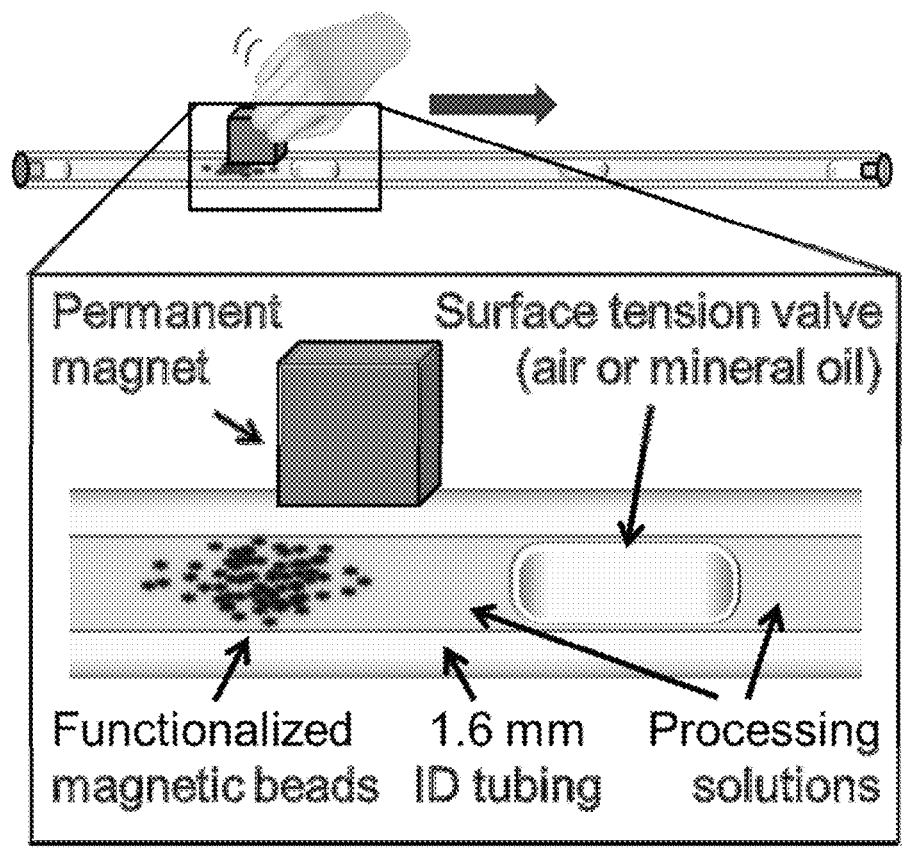
FIG. 8—Design of the prototype extraction method showing three processing solutions held in place in plastic tubing and separated by surface tension valves. Cells are bound to magnetic beads, which are then pulled through a series of washes in a plastic tube using a magnet. The cells are dissociated from the beads following processing.
Figure 9:
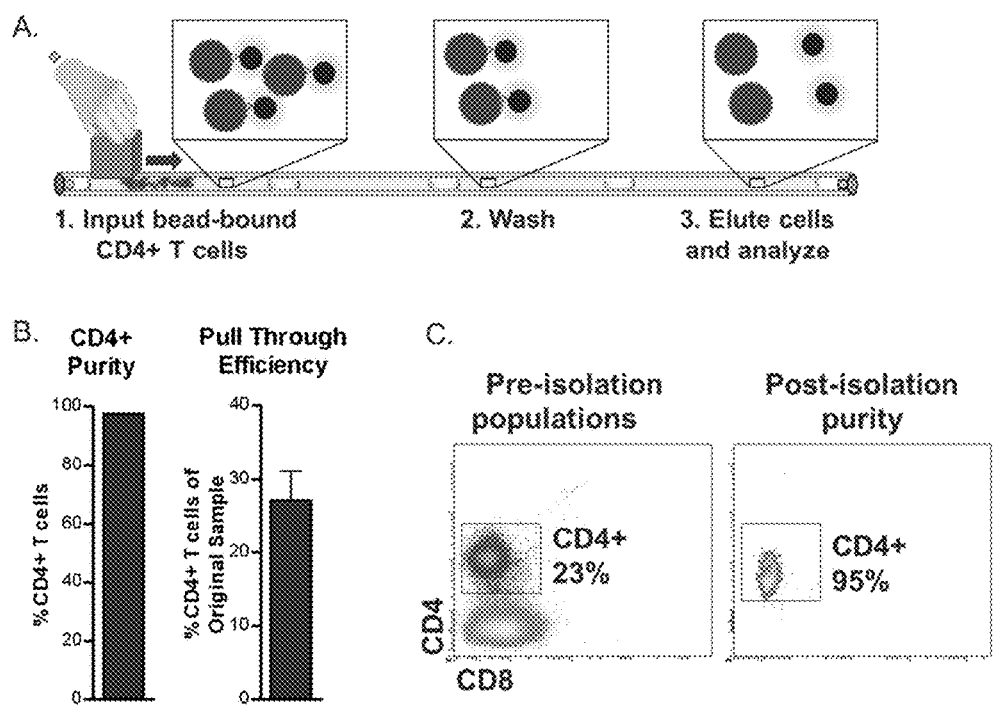
FIG. 9—CD4+ T cell extraction. (A) Diagram of the extraction method and device. (B) Quantification of the CD4+ T cell purity and pull through efficiency. (C) FACS analysis of the pre-isolation populations and post-isolation purity.

Referring to FIG. 1, the user is shown pulling a cube magnet along the sections of tubing joined by plastic pipette tips containing air. The motion of the cube magnet transports magnetic particles across the solution/air interfaces. In the inset, the arrow shows the beads entering the air separating the two liquid solutions. Another embodiment is shown in FIG. 8.

Figure 2:
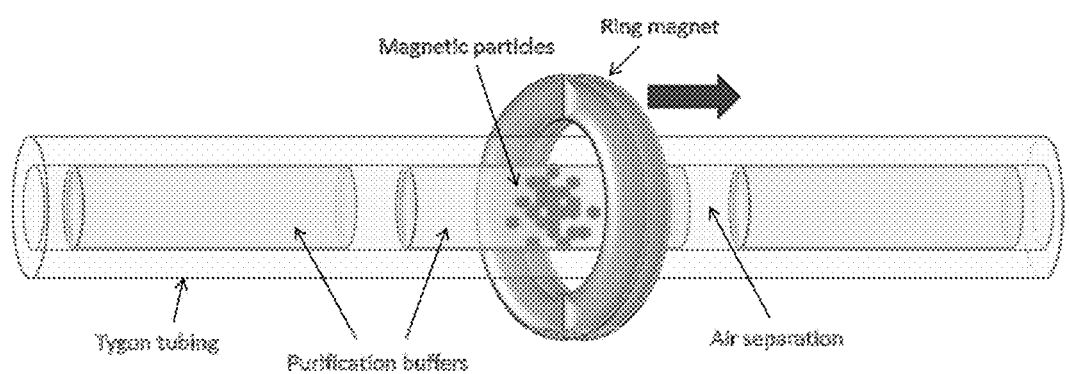
FIG. 2—Magnetic ring device "pull-through" embodiment. Design of the continuous tubing extraction cassette showing individual processing solutions separated by surface tension valves. An external magnet is used to pull whole cells adsorbed to reactant-coated magnetic particles through each processing solution. Following processing, the whole cell is eluted in a final water chamber.

Referring to FIG. 2, a doughnut shaped magnet is manually passed along the tubing and this transports magnetic particles. In the inset, the arrow shows the beads attempting to pass through an air surface tension valve.

Figure 3:
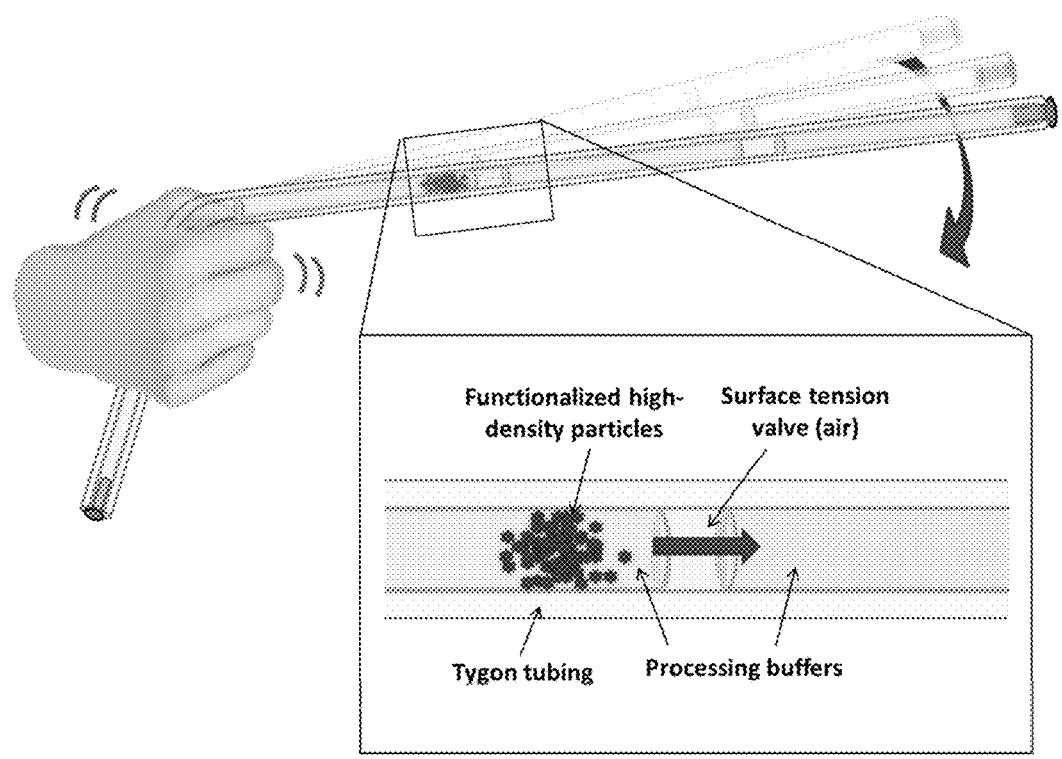
FIG. 3—Low resource processor based on centrifugal force transport of dense beads outward along the extraction cassette.

Referring to FIG. 3, the user is shown driving high density particles down the tubing with hand generated centrifugal force. In the inset, the arrow shows the beads attempting to pass through an air surface tension valve.

Figure 4:
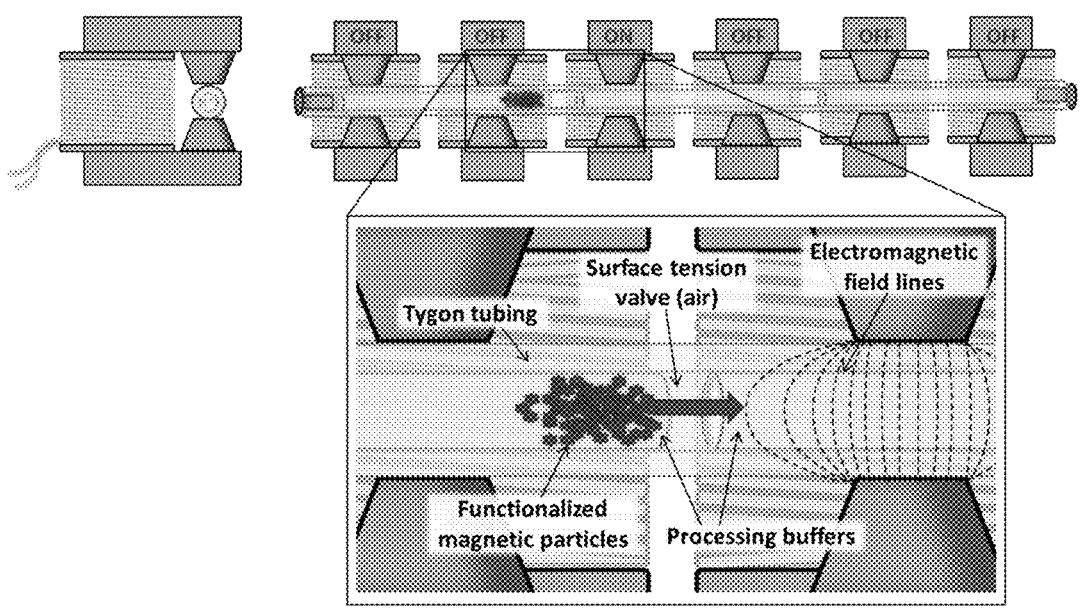
FIG. 4—Automated processor design. Views of an electromagnetic design for transporting magnetic particles from one processing solution to the next. Series of 6 electromagnets arranged in a linear array around a closed tube. Electromagnetics are turned on and off the create transient magnetic fields for pulling the magnet beads across the surface tension interface separating successive processing solutions.

Referring to FIG. 4, a series of c-clamp electromagnets are disposed along the tubing. By subjecting the electromagnets to sequential activation, the magnetic particles are transported along the length of the tubing. In the inset, the arrow shows the beads attempting to pass through a water/air surface tension valve.

Figure 13:
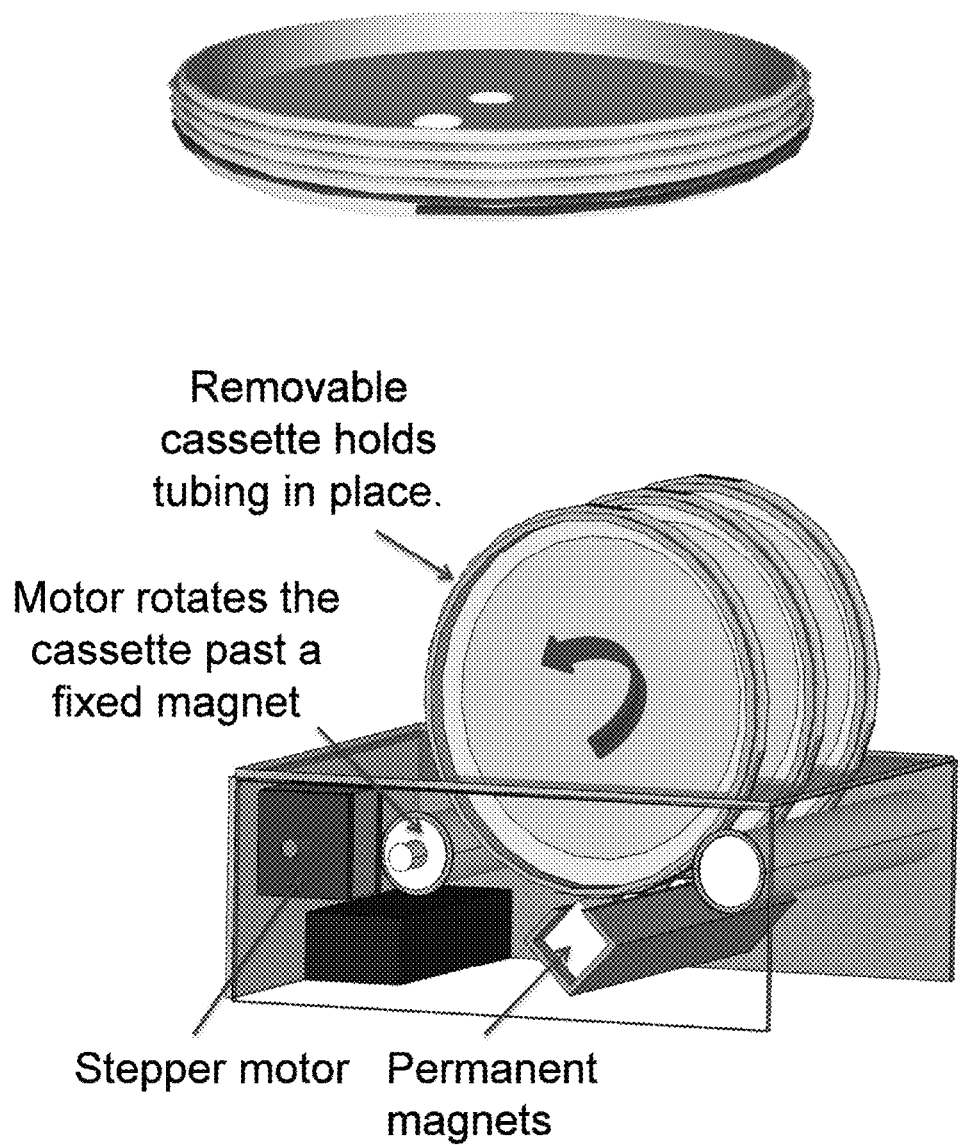
FIG. 13—Example of an automated design based on a fixed magnet and a rotating cassette.

Referring to FIG. 13, an automated device is shown wherein the sample cassette is rotated past a fixed magnet by a motor.

Reaction Chambers. One type of chamber is a reaction chamber. In a reaction chamber, the cell associates with the reactant on the surface of the particle. Such a reaction chamber would be unnecessary in an embodiment where the particles are mixed with a sample prior to introduction into the device. Generally, a reaction chamber will provide suitable conditions under which the reactant on the particle and the cell may interact. The reaction chamber may optionally include agents to inhibit non-specific interactions or to stabilize interactions once achieved.

Processing Chambers. A variety of different types of chambers may be used in accordance with the present invention. It also is possible, where convenient, to have a series of processing chambers. A processing chamber may also be reused in the sense that the flow of the particles may be reversed so that a given chamber is used more than once. The present invention may also utilize multiple processing chambers where different solutions are included therein.

One example of a processing chamber is a pretreatment chamber. It is often the case that reactants, samples or particles will be "pretreated" in such a way as to ensure that the ensuing reaction with the target has a high degree of fidelity, i.e., minimize non-specific attachment. A classic example of a pretreatment is a "blocking" reaction. Non-specific protein-protein interactions are inhibited by pretreating a substrate with a non-specific protein, such as BSA. Similarly, non-specific DNA reactions can be reduced by incubating the probe with a "random" DNA known to lack homology with the probe. Another example of a pretreatment is removing a known cross-reactive species. In the case of isolating CD4+ T cells, it may be desirable to first remove CD14+ monocytes, which also express low levels of CD4. In this case, a pretreatment chamber will precede a reaction chamber.

Another important step when assessing the reaction of biomolecules is to remove non-specifically bound molecules from the reactant. Though achieving the same goal as pretreatment, washing takes place after the exposure of reactant to target. Typically, wash solutions comprise a buffer similar to that used in the target solution, but lacking the target itself. Occasionally, it will be desirable to alter the chemical properties of the wash solution by, for example, changing the salt concentration or pH. Wash chambers would follow a reaction chamber.

An additional chamber may be included into which the species of interest is released during the final extraction process. This chamber's function is to provide the elution step of many extraction processes. This chamber may also effectively function as a concentrating chamber since if its volume is sufficiently small compared to the original sample volume, the number of molecular targets will be higher than in the initial sample, thus effectively concentrating this species.

In some embodiments, it may be desirable to recursively amplify signals relating to binding of target cells to reactants, or to generate more targets for reaction. There are a variety of mechanisms for accomplishing this. However, a common feature will be the need for one or more chambers, prior to or following a reaction chamber, which effect the necessary steps to achieve the amplification.

Finally, in order to increase the efficiency of the process, particles may be retrieved from downstream processing chambers and be returned to an upstream reaction or processing chamber, either by extraction and reintroduction or by reversal of the transport mechanism (e.g., centrifugal force, density or magnetic). By repeating the reaction and/or processing steps, one can increase both the signal and specificity of binding and detection.

Figure 5:
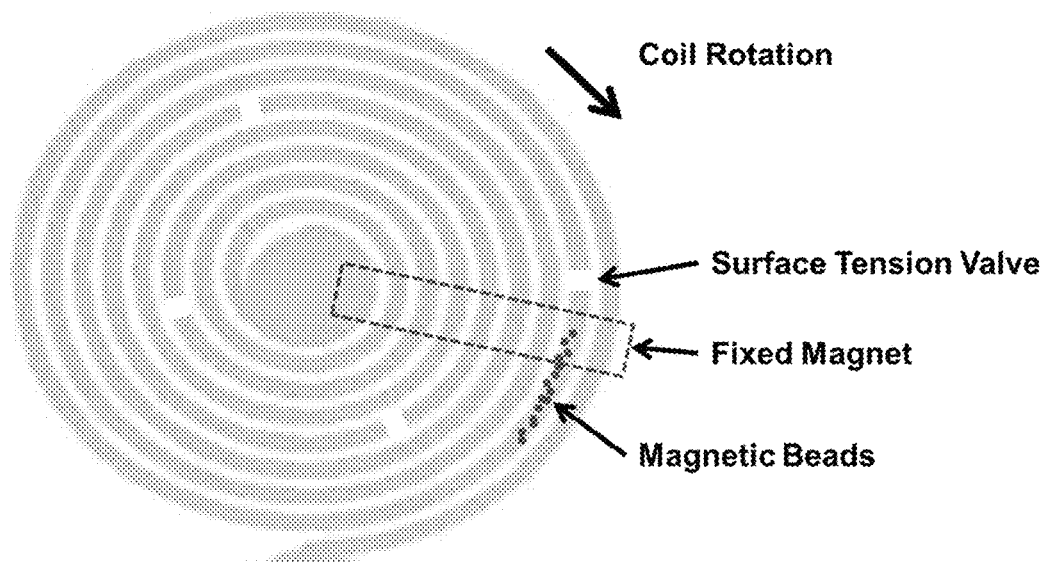
FIG. 5—Automated processor design. Top view of a coiled processor design. Fluid filled tubing contains four surface tension valves separating the five processing solutions. The coil is rotated under a fixed magnet and the magnetic beads are moved by the magnetic field through a series of processing solutions.

Thus, FIGS. 1-4 and 8 show embodiments of chambers arrayed in linear array. Tubing may also be flexible and as shown in FIG. 5 an additional embodiment may be a flat coiled design that shows the tubing arrayed a coil that slowly rotates to pull the magnetic particles from one chamber to the next.

3. Surface Tension Valves

An important aspect of the invention is the use of surface tension valves to separate the tubing into discrete chambers. These surface tension valves allow flexibility in the composition of the processing fluids and the movable substrate.

In essence, the surface tension valve is simply a nonreactive gas or liquid that separates various sections of the device by creating a stable interface with the fluids that make up the various chambers. Important aspects of the gas or liquid include low vapor pressure or low surface tension, which are defined as having a vapor pressure significantly less than 1 kPa and a surface tension between 2 and 100 mN/m, including about 72 for air/water, about 50 for water/mineral oil, and about 3.3 for benzyl alcohol/water (values are from Handbook of Organic Solvents) (Lide, 1995) (incorporated by reference). Examples of appropriate gases include air, carbon dioxide, nitrogen, argon, helium, or sulfur hexafluoride. Liquids include Mineral oil, Dodecane, 1-Dodecene, Tridecane, Methyloleate, Acetophenone, Propyl Benzoate, or 1-Methylnaphthalene. Also, addition of certain materials can alter the surface tension interface, e.g., Tween® can lower the surface tension.

There a number of ways that transport of the particles across the surface tension valve can be achieved as illustrated in FIGS. 1-5 and 8. For example, an external permanent magnet, an external movable electromagnet, centripetal force applied by tube motion around one end, and density driven (i.e., a heavy particle falling under gravity or a buoyant particle moving upward in less dense fluid).

4. Particles

The particles for use in the present invention combines the functionalities of preferential binding to a class of molecules or to a select target of interest, susceptible to transport by external force (e.g., magnet, or density differences), and small size to increase reaction efficiencies.

The particles may be synthesized using a variety of materials, such as metal, ceramic, glass, or a polymer. In particular, the particles are magnetic or paramagnetic for embodiments where magnetic fields are employed. In embodiments where centrifugal force is applied, the particles should have a density of >1.

Commercially available particles include those provided by SIGMA-ALDRICH and include polystyrene, polystyrene monodisperse, magnetic, melamine resin, melamine resin-carboxylate modified, polymethacrylate and silica (including beads coated with any of the foregoing substances).

Figure 6:
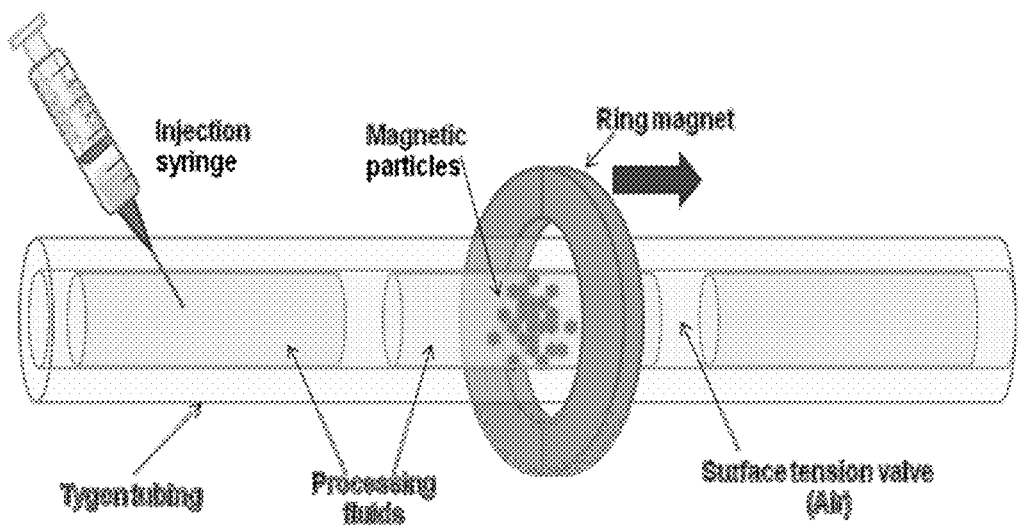
FIG. 6—Low resource point-of-care extraction processor illustrating the use of surface tension valves (in this case liquid/air interfaces) to separate liquid processing steps. A biological sample is injected into the left chamber (syringe) followed by movement of reactant-coated magnetic beads from this chamber into the second using an external ring magnet. In this illustration, the captured material is released in the final chamber on the right.
Figure 7:
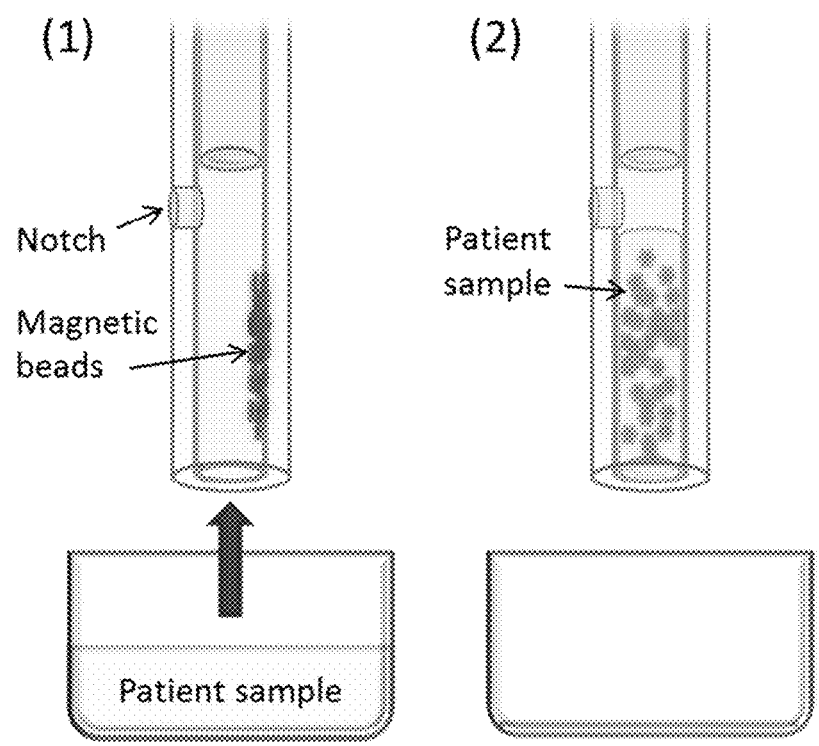
FIG. 7—Extraction cassette loading design. Method of introducing a patient sample into one end of an extraction cassette. (1) the end of the cassette is lowered into the patient sample and capillary action draws the patient sample up into one end of the cassette (2) where it interacts with magnetic beads dried on the inner surface of the tube. An external magnet is then used to transport the beads through the surface tension valves and processing solutions contained in the upper section of the tubing.

Introduction of the particles/sample into the cassette may be achieved in a number of methods. FIG. 6 illustrates injection of a sample through the wall of Tygon tubing. Particles may be mixed with the sample before injection or particles may be already present either in suspension or dried within the first section of tubing. FIG. 7 illustrates a second embodiment for loading particles/sample through capillary action. In this embodiment, capillary forces present in small diameter tubes result in the drawing up of the sample into the first section of the cassette. Particles may be mixed with the sample before being drawn up or dried along the first section of tubing in which case they are released when they come into contact with the advancing fluid. Transport of particles among the following chambers proceeds as described above.

5. Kits

According to the present invention, there are provided kits containing the devices described above. Generally, kits comprise separate vials or containers for the various reagents, such as particles, reactants, and detection reagents—either as liquids or as lyophilized solids. In the case of the latter, suitable solvent may be included, such as water, ethanol, various buffer solutions, and the like. The reagents may also be provided in the device in a ready-to-use form, i.e., with chambers and surface tension valves already established in the device. The device, particles, reactants and/or reagents may be disposed in vials or containers held in blow-molded or injection-molded plastics, or in tubing coiled within a flat circular cassette.

B. Reactants and Targets

Another important aspect of the invention is the reactants that are disposed on the surface of the particles, and the targets with which these reactants interact. By reactant, it is not necessary that the material interact in any particular type of way. Rather, any physical interaction that permits association of reactant with the target cell is envisioned, such as covalent, non-covalent, electrostatic, hydrostatic, or ionic. For example, by coating a particle with an antibody, one can absorb cells expressing the antigen for said antibody to the particle to the exclusion of other biomolecules. Molecules that coordinate metals, in particular heavy metals, are also envisioned as reactants. Nickel and cobalt are in particular contemplated. One can also use non-specific binding to pull out a more general class of compounds based simply on their relative interaction with the reactants.

The whole cells may be any type of cell. The reactants can be any of a wide variety of biomolecules including proteins or nucleic acid aptamers. Other reactants include amino acids and small organic molecules. For two nucleic acids, the binding interaction will generally be characterized by hybridization, achieved by homologous base pairing. For one or more protein molecules, the interaction will generally be the formation of protein-ligand complexes which are reliant on the complementary structure and charge of the component molecules, such as antibody-antigen interactions and receptor-ligand interactions. Various types of molecules suitable for use in accordance with the present invention are described below.

Nucleic acids, proteins, small molecules, and other targets may be detected as described below as a means of detecting an isolated whole cell. They may also be detected apart from a whole cell as a second analyte for multiplex detection.

1. Cells

Whole cells may be of any origin, including protists, animals, or plants. The cells may be living or fixed at the time of processing. Protists may be of the genus *Plasmodium, Babesia, Leishmania, Giardia,* or *Trypanosoma*. Animal cells may be mammalian, preferably human. Cells may be CD4+ T cells, virus-infected cells, parasite-infected cells, cancer cells, or blood cells. Cells may be processed from whole blood specimens. The whole blood specimen may be fresh.

The cells in the sample may be quantified using a known ratiometric particle for determining cell counts. Absolute cell counts and ratiometric cell counts may be determined using a spectrophotometer.

2. Nucleic Acids

The term "nucleic acid" is well known in the art. A "nucleic acid" as used herein will generally refer to a molecule of DNA, RNA or a derivative or analog thereof, including synthetic molecules. Nucleic acids are also defined as molecules containing a series of naturally-occurring purine or pyrimidine bases. The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to both single-stranded and double-stranded molecules, the latter being substantially or fully complementary to each other. A nucleic acid may even encompass a triple-stranded molecule. As used herein, a single stranded nucleic acid may be denoted by the prefix "ss," a double-stranded nucleic acid by the prefix "ds," and a triple stranded nucleic acid by the prefix "ts."

(b) DNA

DNAs are defined as nucleic acids containing adenine "A," guanine "G," thymine "T" and cytosine "C." DNA molecules, both single- and double-stranded, may be utilized in accordance with the present invention. DNAs may comprise coding sequences or non-coding sequence, and genomic sequences or cDNAs, synthesized strands homologous to the target of interest. DNA "arrays"—collections of DNAs that represent a group of selected probes.

(c) RNA

RNAs are defined as nucleic acids containing A, G, uracil "U" or C. Both single- and double-stranded RNAs, may be utilized in accordance with the present invention. Because of their labile nature, additional steps must be taken to preserve the integrity of RNA containing samples. In particular, the ubiquitous presence of RNAses requires the use of RNAse inhibitors such as DEPC.

3. Proteins

In another embodiment, the probe may be a proteinaceous compound. There are wide varieties of protein-protein interactions; however, proteins also bind nucleic acids, metals and other non-proteinaceous compounds (e.g., lipids, hormones, transmitters). Some examples of protein that may be used as either targets or probes are listed below.

(a) Antibodies

Antibodies may be used as probes for unknown molecules, or they maybe the target for reaction with a known probe. The antibodies may be either polyclonal or monoclonal in origin. Method for preparing antibodies are well known to those of skill in the art and need not be discussed here. Antibodies may be fixed to the filament support using standard techniques.

Obviously, identifying antibodies that bind to certain target molecules is an important goal that could be accomplished by the present invention. However, the present invention also permits the screening of samples for the presence of antibodies. For example, a particle might contain a variety of bacterial and viral antigens, which could assist in diagnosis of infectious disease by identifying relevant antibodies in an affected subject.

(b) Enzymes

Enzymes are proteins that facilitate the modification of a wide variety of compounds including nucleic acids, other proteins, lipids, sugars, steroids and many other compounds. Particular types of assays contemplated include identifying inhibitors of enzymes that bind to, but are not processed by, the enzyme. Alternatively, identifying compounds that are bound by an enzyme may assist in design of pro-drugs that are processed by an enzyme.

(c) Receptors

Receptors are molecules that facilitate signaling processes by binding their cognate ligand moieties. Once bound, the receptor will then perform some other function (enzymatic, intracellular translocation, cell permeability) that effects the signaling. Identifying molecules that block receptor function, or mimic the natural ligand, can be accomplished using the present invention.

(d) DNA-binding proteins

Another important class of proteins is the DNA binding proteins. These proteins include polymerases, helicases, ligases, and transcription factors. The proteins have varying degrees of DNA sequence specificity can be assessed for ability to bind varying DNA sequences. Conversely, providing a DNA sequence as a probe, once can identify unknown binding proteins with specificity for that sequence.

4. Small Molecules and Other Targets

A wide variety of "small molecules" can be examined for their ability to interact to a given reactant. These libraries comprise non-protein and non-nucleic acid molecules. Alternatively, libraries can be constructed around particular "pharmacores" that are believed to provide basic structural features necessary for a particular drug to function.

Also, compounds such as liquids, carbohydrates, metals, and toxins may be assayed using the devices and methods of the present invention.

5. Labels

In various embodiments, it may desirable to label particles, reactant, or target molecules. Examples of labels include paramagnetic ions, radioactive isotopes, chemiluminescent compounds, fluorophores, chromophores, NMR-detectable substances, and X-ray imaging compounds.

Paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

Radioactive isotopes include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often preferred for use in certain embodiments, and technicium$^{99m}$ and/or indium$^{111}$ are also often preferred due to their low energy and suitability for long range detection.

Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Enzymes (an enzyme tag) that will generate a colored product upon contact with a chromogenic substrate may also be used. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

C. Definitions

The terms a or an, as used herein, are defined as one or more than one.

The term plurality, as used herein, is defined as two or more than two.

The term another, as used herein, is defined as at least a second or more.

The terms including and/or having, as used herein, are defined as comprising (i.e., open language).

The term coupled, as used herein, is defined as connected, although not necessarily directly.

The term approximately, as used herein, is defined as at least close to a given value (e.g., preferably within 10% of, more preferably within 1% of, and most preferably within 0.1% of).

The term substantially, as used herein, is defined as at least approaching a given state (e.g., preferably within 10% of, more preferably within 1% of, and most preferably within 0.1% of).

The phrase "any integer derivable therein," as used herein, is defined as an integer between the corresponding numbers recited in the specification, and the phrase any range derivable therein is defined as any range within such corresponding numbers.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Extraction of CD4+ T Cells

Figure 10:
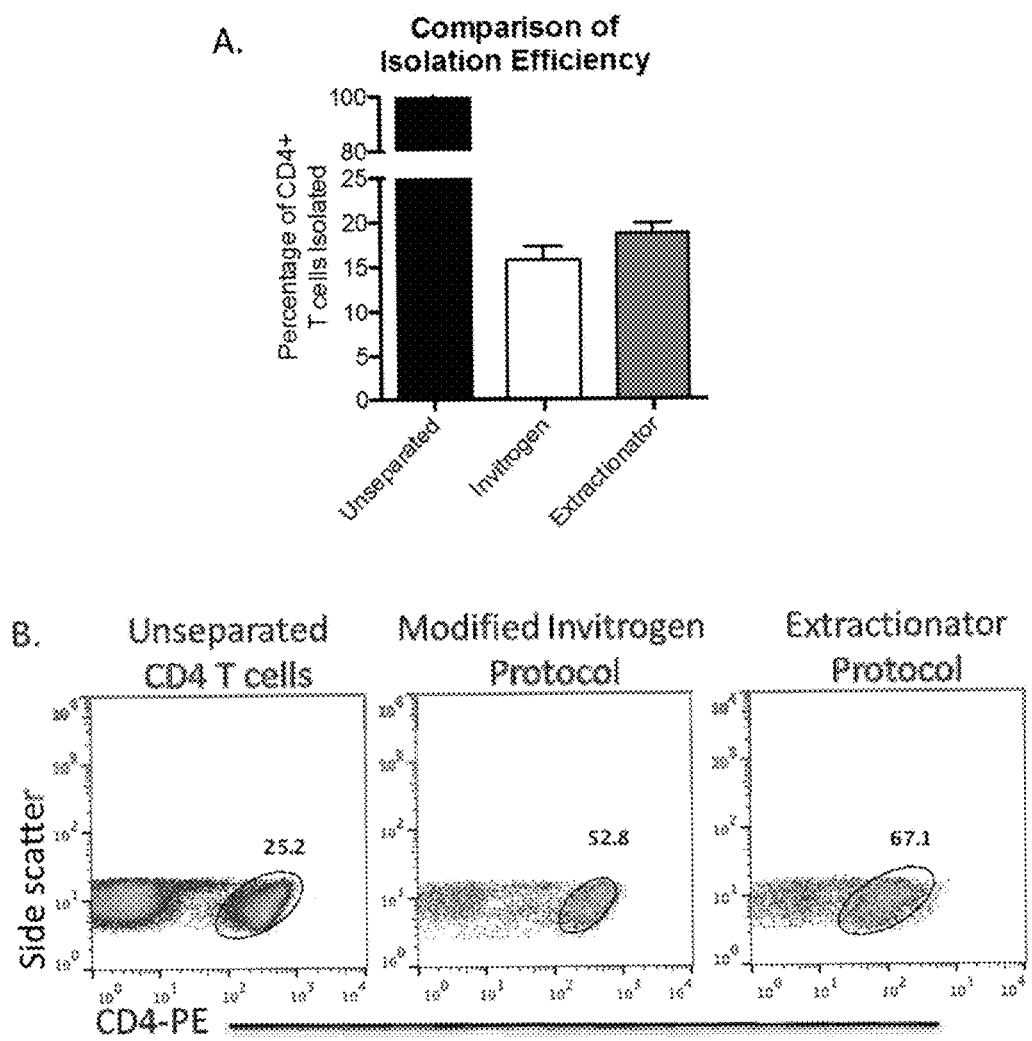
FIG. 10—CD4 extraction: high isolation efficiency versus standard separation protocol. (A) Comparison of isolation efficiency. (B) Comparison of isolation purity. Gated percentages indicate percent CD4+ T cells of parent lymphocyte gate.

Single-cell suspensions were prepared from PBMC. Three sets of three samples were prepared: unseparated cells, cell subjected to separation using a protocol modified from Invitrogen's Dynabeads human CD4 T cell isolation product, and cells subjected to separation using the extraction cassette. The isolation efficiency and purity were determined for each sample preparation (FIG. 10). The low yield and purity compared to unseparated cells was likely due to the use of insufficient quantities of separation beads for a very concentrated cell preparation. Additionally, the presence of CD14+ monocytes that express low levels of CD4 may affect sample purity. Therefore, the ideal volume of magnetic separation beads requires optimization. High yield (119% compared to standard) was observed in comparison with a typical isolation performed in eppendorf tubes.

Figure 12:
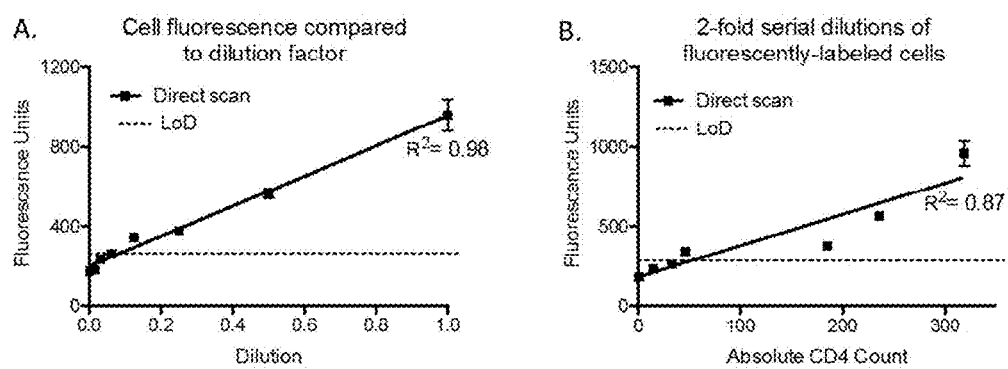
FIG. 12—Enumeration of fluorescently-labeled cells using a spectrophotometer. PBMC were labeled with anti-CD4-PE antibodies and 2-fold serial dilutions were prepared. Cells were counted using flow cytometry and total fluorescence was measured on a laboratory spectrophotometer. (A) Linear regression of the 2-fold serial dilution vs. fluorescence. (B) Linear regression of the cell count versus fluorescence.

Fluorescently-labeled cells may be enumerated using a spectrophotometer. Two sets of PBMC were identically labeled with anti-CD4-PE antibodies and two-fold serial dilutions were prepared. The cells in one set of dilutions were counted using flow cytometry and the cells in the other set of dilutions were measured on a laboratory spectrophotometer to determine total fluorescence. The two-fold dilutions were found to have a very high $R^2$ value, indicating a high level of accuracy in dilution preparation (FIG. 12A). The cell count comparison also had a good $R^2$ value, but was subject to some variation due to the nature of the indirect comparison—fluorescence vs. a calculated value for cell count (FIG. 12B). The limit of detection was found to be appropriate for detecting about 100-200 cells, which is clinically relevant for both initiation of ART as well as ART maintenance.

Example 2

Phantom CD4 Bead Development

Phantom CD4 cells will be used as cell surrogates in the enumeration studies. The cell surrogate beads will be FITC doped, will have CD4 protein on their surface, and will be bound and labeled by the anti-CD4 magnetic beads as well as the anti-CD4 fluorescent antibodies (PE). The beads will provide a measure of extraction efficiency as they are isolated and measured alongside fluorescently-tagged CD4+ T cells (PE). The number of phantom cells that are present at the beginning of the extraction is known, and the number of beads that are successfully extracted will be measured. As two different labels are used to separately measure the number of real target cells and the number of phantom cells extracted using the device at the same time, this will provide a phantom cell to CD4+ T cell (FITC:PE) ratio for determining the number of CD4+ T cells in the original sample based on the number of CD4+ T cells that were extracted. The phantom cells will also serve as a QA/QC test.

Figure 11:
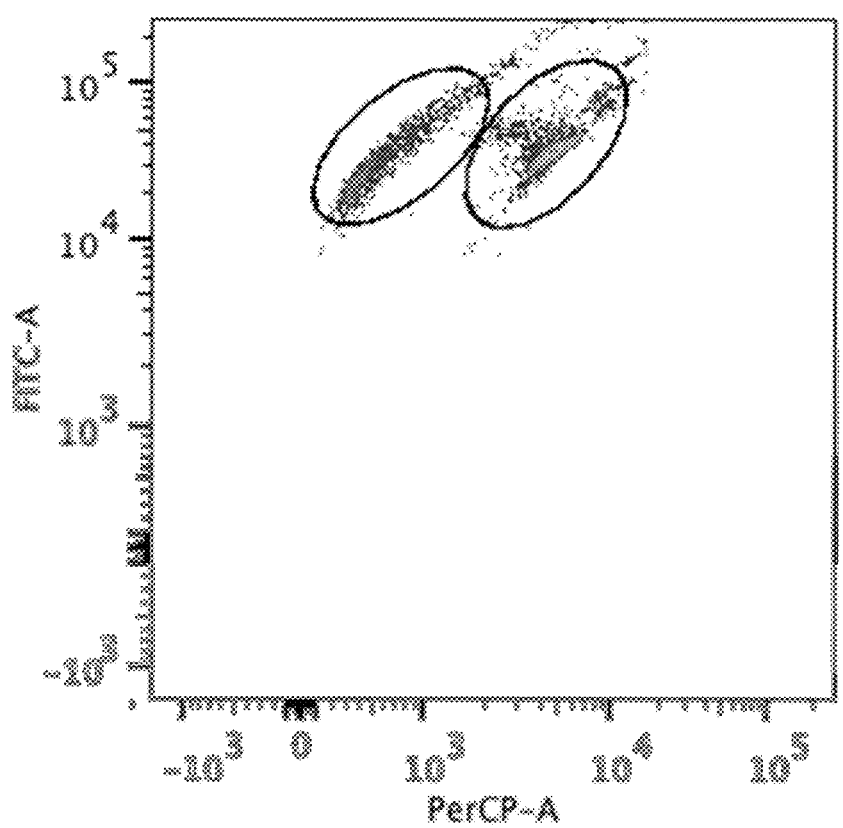
FIG. 11—Phantom CD4 cells. Cell surrogate beads will be bound and labeled by the anti-CD4 magnetic beads as well as the anti-CD4 fluorescent antibodies (PE). The circle on the left represents the phantom CD4 cells. The circle on the right represents commercial (Invitrogen) counting beads.

In one embodiment, the beads may be 1 µm polystyrene beads coated with gold, doped with FITC, and bound with CD4 protein. An example of such beads is provided in FIG. 11, where the circle on the left represents phantom cells and the circle on the right represents commercial (Invitrogen) counting beads. The phantom cells will be optimized for brightness using flow cytometry and spectrophotometry before binding CD4 protein. The beads may be prepared with 1, 2, or 3 coats of gold.

* * *

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
Avison, In: *Measuring gene expression*, Taylor & Francis, NY, 2007; 324, 2007.
Beuselinck et al., *J. Clinical Microbiol.*, 43(11):5541-5546, 2055.
Chen et al., *Biomed. Microdevices*, 12(4):705-719, 2010.
Coiras et al., *J. Med. Virol.*, 69(1):132-144, 2003.
Hagan et al., *Lab. Chip.*, 11(5):957-961, 2011.
Handbook of Solvents, Lide (Ed.), CRC Press, 1-565, 1995.
Monteiro et al., *J. Clinical Microbiol.*, 35(4):995-998, 1997.
Niemz et al., *Trends Biotechnol.*, 29(5):240-250, 2011.
Price et al., *Lab. Chip.*, 9(17):2484-2494, 2009.
Radstrom et al., *Mol. Biotechnol.*, 26(2):133-146, 2004.
Wilson, *Appl. Environ. Microbiol.*, 63(10):3741-3751, 1997.
Yamada et al., *J. Virol. Methods*, 27(2):203-209, 1990.

What is claimed is:

1. A method of detecting a human whole cell in at least one sample comprising:
    (a) providing a device comprising a plurality of sequential chambers connected by tubing, each of said sequential chambers comprising a fluid and separated by gas-based surface tension valves;
    (b) introducing into a first chamber of the plurality of sequential chambers said sample and a particle comprising a surface reactant, wherein said surface reactant binds to the at least one human whole cell said particle, wherein said particle is 0.1 micrometers to 4 mm in diameter;
    (c) transporting the particle bound to said at least one human whole cell from said first chamber of the plurality of sequential chambers into at least a second chamber of the plurality of sequential chambers through said tubing connecting said first and second chambers of the plurality of sequential chambers; and
    (d) detecting the presence of said at least one human whole cell in said second or a subsequent chamber.

2. The method of claim 1, wherein said particle is a magnetic particle, a paramagnetic particle or a non-magnetic particle having a relative density of >1 or <1 compared to said fluid in said first chamber.

3. The method of claim 2, wherein transporting comprises passing a magnetic field along said tubing or subjecting said tubing to distinct intermittent magnetic fields to effect movement of said particle.

4. The method of claim 2, wherein said non-magnetic particle having a relative density of >1 compared to said fluid in said first chamber is transported by density driven transport.

5. The method of claim 1, wherein transporting comprises applying centrifugal force to said device such that said particle is transported through said plurality of sequential chambers.

6. The method of claim 1, wherein said reactant is an antibody, an aptamer, or a cell surface receptor ligand.

7. The method of claim 1, wherein introducing comprises injecting said particles through a wall of said first chamber.

8. The method of claim 1, wherein introducing comprises movement of the sample containing the at least one human whole cell into said first chamber by capillary action.

9. The method of claim 1, wherein said plurality of sequential chambers comprise at least three chambers.

10. The method of claim 1, further comprising reversing the transport of said particle to reintroduce said particle into at least one of the plurality of sequential chambers.

11. The method of claim 1, wherein said gas-based surface tension valves comprise a non-reactive gas having low vapor pressure and/or low surface tension.

12. The method of claim 1, wherein said first chamber further comprises a known quantity of phantom cells.

13. The method of claim 1, wherein said surface of said particles further comprises a known quantity of phantom cells.

14. The method of claim 1, wherein said first chamber further comprises a second particle having a second reactant on its surface, said sample further comprises an analyte that reacts with said second reactant.

15. The method of claim 14, wherein said analyte is a protein, a polypeptide, a lipid, a carbohydrate, a nucleic acid, a heavy metal, an organochemical compound, a bacterium, a virus, or a fungal cell.

16. The method of claim 14, wherein said second reactant is an antibody, an antigen, a chelating agent, a lipid, a carbohydrate, a metal, an organochemical compound, an enzyme substrate, a nucleic acid, or a second cell.

* * * * *

UNITED STATES PATENT AND TRADEMARK OFFICE
CERTIFICATE OF CORRECTION

PATENT NO. : 9,869,675 B2
APPLICATION NO. : 14/201097
DATED : January 16, 2018
INVENTOR(S) : Rick Haselton et al.

Page 1 of 1

It is certified that error appears in the above-identified patent and that said Letters Patent is hereby corrected as shown below:

In the Claims

In Claim 1, Column 17, Line 50, delete "said particle".

Signed and Sealed this
Twenty-sixth Day of June, 2018

Andrei Iancu
*Director of the United States Patent and Trademark Office*